Figure 2:
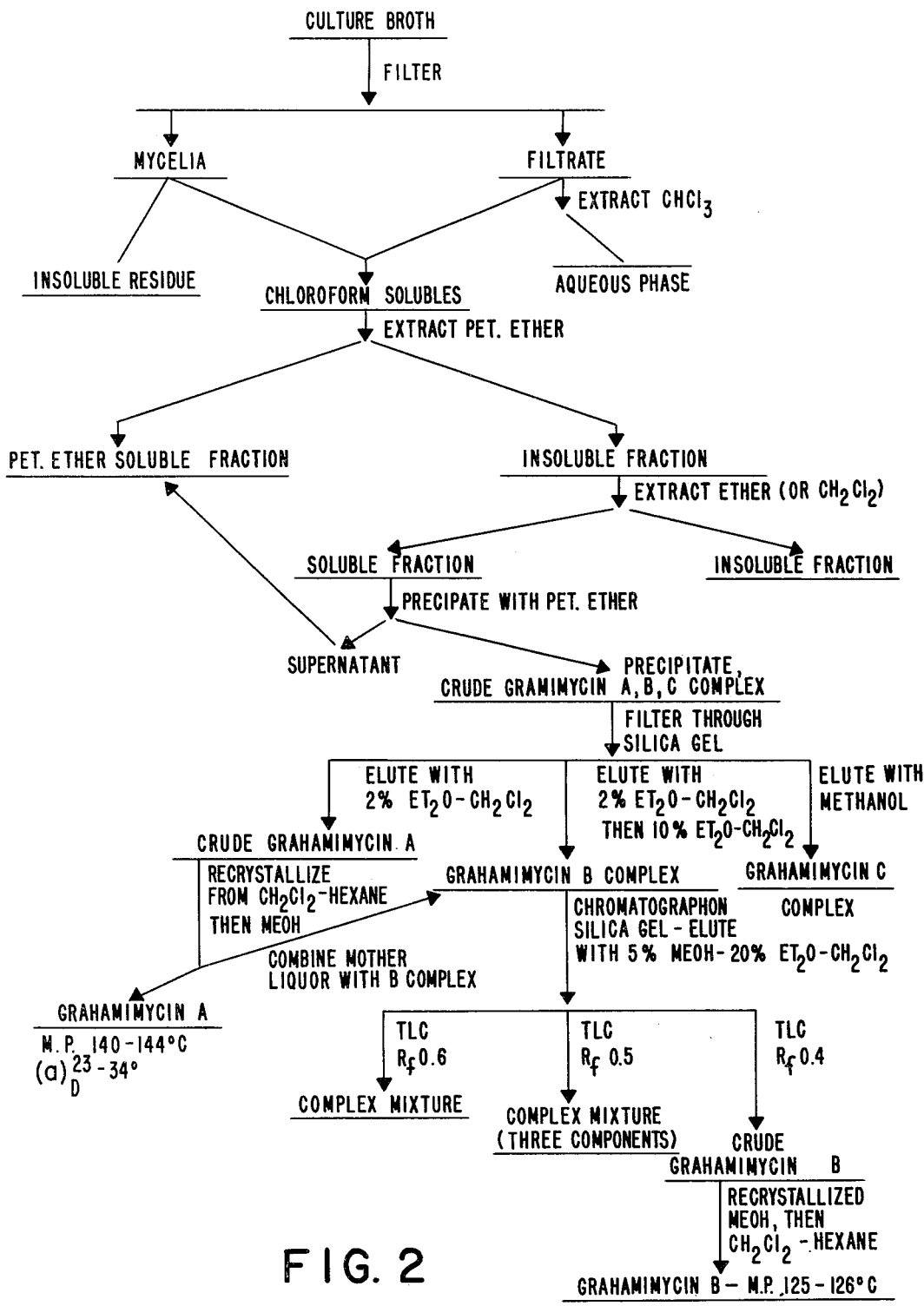

United States Patent [19]

Gurusiddaiah et al.

[11] 4,239,690
[45] Dec. 16, 1980

[54] **ANTIBIOTICS PRODUCED BY *CYTOSPORA SP.* W.F.P.L. 13A**

[75] Inventors: Sarangamat Gurusiddaiah; Robert C. Ronald; James A. Magnuson; Bruce A. McFadden, all of Pullman, Wash.

[73] Assignee: Washington State University Research Foundation, Pullman, Wash.

[21] Appl. No.: 87,177

[22] Filed: Oct. 22, 1979

Related U.S. Application Data

[62] Division of Ser. No. 882,492, Mar. 1, 1978.

[51] Int. Cl.³ .......................................... C07D 321/00
[52] U.S. Cl. ................................. 260/340.2; 435/124
[58] Field of Search ....................................... 260/340.2

[56] References Cited

U.S. PATENT DOCUMENTS

| | | | |
|---|---|---|---|
| 3,562,313 | 2/1971 | Cross et al. ................... | 260/340.2 X |
| 4,165,321 | 8/1979 | Harris et al. ...................... | 260/340.2 |

FOREIGN PATENT DOCUMENTS

| | | | |
|---|---|---|---|
| 40-26533 | 11/1965 | Japan .................... | 260/340.2 |
| 50-69088 | 9/1975 | Japan .................... | 260/340.2 |
| 81179 | 10/1956 | Switzerland ........... | 260/340.2 |

*Primary Examiner*—Ethel G. Love

*Attorney, Agent, or Firm*—Jones, Tullar & Cooper

[57] ABSTRACT

When *Cytospora sp.* is subjected to aerobic fermentation a number of new antibiotics are produced. Methods of production, recovery and purification of these antibiotics are described and some of their antimicrobial properties are described. One of the new antibiotics discovered (Grahamimycin A) corresponds to the formula:

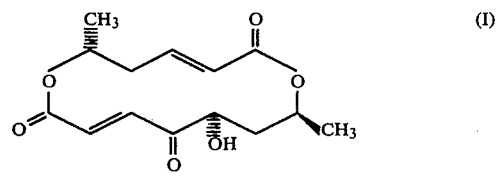

Another (Grahamimycin B) corresponds to the formula:

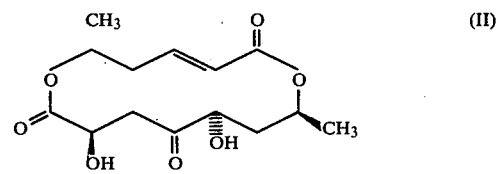

4 Claims, 4 Drawing Figures

ANTIBIOTIC ACTIVITY IN CULTURE FILTRATE OF *CYTOSPORA SP.* DURING AEROBIC GROWTH.

EXTRACTION AND SEPARATION OF ANTIBIOTIC SUBSTANCES FROM FERMENTATION CULTURES OF *CYTOSPORA SP.*

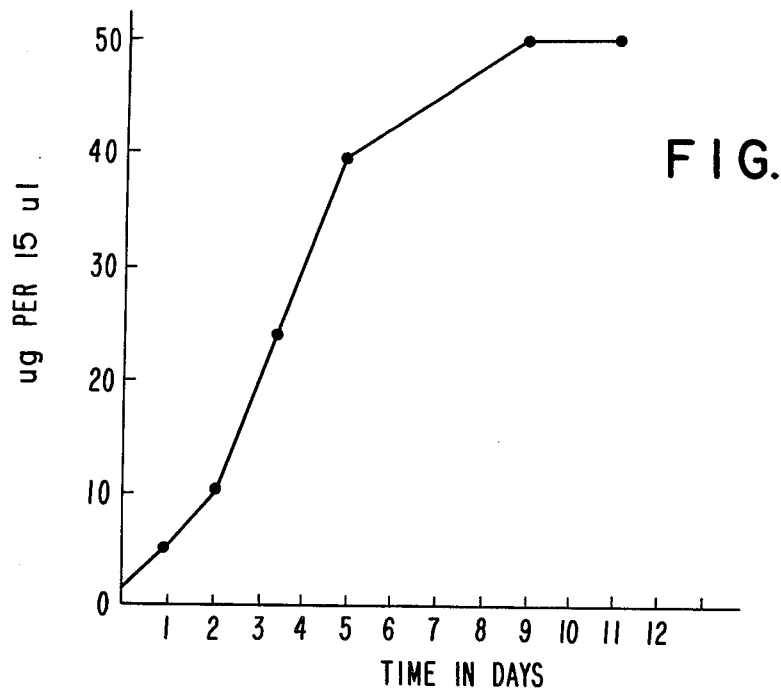
ANTIBIOTIC ACTIVITY IN CULTURE FILTRATE OF <u>CYTOSPORA SP.</u> DURING AEROBIC GROWTH.
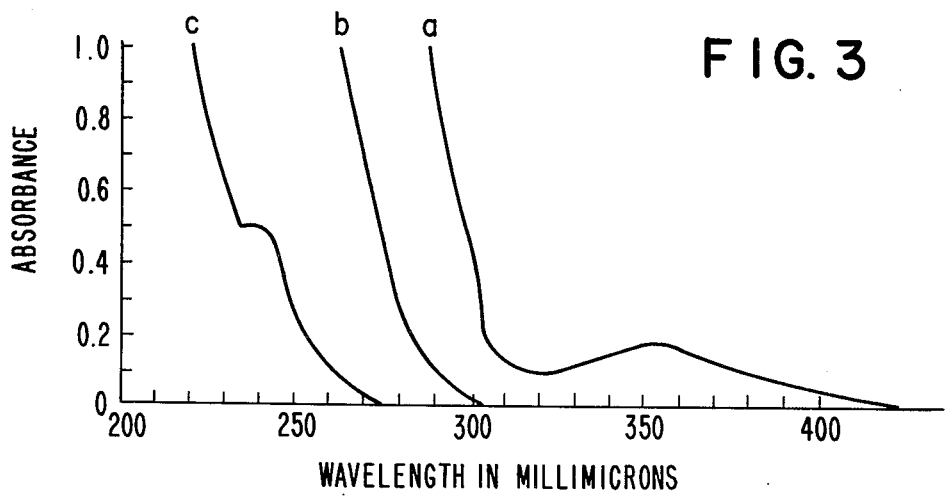
ULTRAVIOLET SPECTRUM OF GRAHAMIMYCIN A IN THREE DIFFERENT CONCENTRATIONS: a) 1.5 MG/ML, b) 0.15 MG/ML, AND c) 0.015 MG/ML.

EXTRACTION AND SEPARATION OF ANTIBIOTIC SUBSTANCES FROM FERMENTATION CULTURES OF CYTOSPORA SP.

ANTIBIOTICS PRODUCED BY CYTOSPORA Sp. W.F.P.L. 13A

This is a division of application Ser. No. 882,492, filed Mar. 1, 1978.

BACKGROUND OF THE INVENTION

The search for new antibiotics produced by soil microorganisms has encompassed the screening of various genera of bacteria, high bacteria and fungi including many strains within each species.

Among the microorganisms that have not received much attention is a fungus which belongs to the form class Deuteromycetes (or Fungi Imperfecti), form order Sphaeropsidales, form family Sphaeropsidaceae and the form genus Cytospora sp. W.F.P.L. (Western Forest Products Laboratory in Vancover, B.C., Canada) 13A.

While screening for new antibiotics from plant pathogenic fungi strong antimicrobial activity was observed in agar plate cultures of at least ten genera of fungi not previously reported to produce any antibiotics.

U.S. Pat. No. 3,151,038 to Gray describes a process for the production of proteins and while Cytospora sp. is mentioned there is no reference to Cytospora sp. W.F.P.L. 13A and the process conditions employed are significantly different.

MacMillian et al, *J.C.S. Perkin* 1, 14, 1487-1493 (1973) describe colletoketol, which appears to be a stereoisomer of Grahamimycin A, produced herein. Colletoketol was produced by the fermentation of the plant pathogen, *Colletotrichum capsici.*

DESCRIPTION OF THE INVENTION

This invention relates to antibiotics produced by aerobic fermentation of Cytospora sp. W.F.P.L. 13A in the presence of a suitable carbon source, with aeration. While aeration is essential for the production of the antibiotic, the donor fungus grows equally well under anaerobic conditions.

Cultivation of the Cytospora sp. W.F.P.L. 13A culture preferably takes place in nutrient media at a temperature of about 20° to about 30° C. and preferably about 24° to about 27° C. and under submerged aerobic conditions with agitation. Suitable nutrient media are described hereinafter. If excessive foaming is encountered during fermentation, antifoam agents such as silicone oils may be added to the medium. The pH of the fermentation tends to decrease with time, and buffering is usually not necessary, but if variations are encountered, a buffering agent such as calcium carbonate can be employed. Aeration of the media for submerged growth is preferably maintained at a rate of about 0.2 to 0.3 volumes of air per volume of broth per minute. Agitation may be maintained by means of agitators generally familiar to those in the fermentation industry. Aseptic conditions must, of course, be maintained in the transfer of the microorganisms and throughout its growth.

An inoculum for the preparation of the antibiotics can be obtained from known cultures of Cytospora sp. W.F.P.L. 13A such as the stock cultures described hereinafter. The culture may be used to inoculate either shaker flasks or inoculum tanks, or alternatively, the inoculum tanks may be seeded from the shaker flasks. The growth of the microorganism usually reaches its maximum in about 8-10 days. However, variation in equipment used, aeration, rate of stirring etc. may affect the speed with which maximum growth is reached. In general, the fermentation is conducted until substantial antimicrobial activity is imparted to the medium, a period of from about 7 to about 9 being sufficient for most purposes.

The process of antibiotic production is conveniently followed during fermentation by biological assay of the broth employing the susceptible organism *Pseudomonas nigrifaciens* in a zone inhibition assay technique as described hereinafter.

The desired antibiotic products are present in the culture filtrate, as well as in the culture medium and may be isolated by filtration of the culture medium followed by extraction with a suitable solvent, for example, as set forth in the flow chart in FIG. 2. Further separation and purification may be carried out by means of chromatography using an adsorption column, for example, silica gel, and elution solvents.

Thin-layer chromatography employing silica gel is a useful tool for analyzing the antibiotics produced in the culture and the composition of crude and purified materials extracted from fermentation broths.

Cytospora sp. W.F.P.L. 13A, which grows on lodge pole pine as a saprophyte, is described as follows:

a. MORPHOLOGY OF CYTOSPORA Sp. W.F.P.L. 13A

Cytospora sp. W.F.P.L. 13A produces cream white to hyaline, moderate to profusely branched, multiseptate mycelia on agar cultures. On several media the older mycelia turn dark green to brown in color. This organism which produces no pigment on most media will produce a dark green to brown pigment when grown in a medium containing potato extract. No perfect stages of this fungus are known. After three to four weeks of growth on potato dextrose agar (PDA) at 23°-24° C., or two weeks of growth on malt-yeast extract agar (MYA) at 23°-24° C., the fungus produces abundant stromatic bodies. These stromata are dark brown to black, tough, leathery to brittle, carbonaceous, and measure 2-5 mm across. Stromata are glabrous or sometimes covered with velvety-woolly white mycelia and a few multi-cellular, brown whiplike appendages on the dark brown pseudoparenchymatous stromatic tissues. Older stromata exude one or two drops of light-yellow to amber-colored viscous fluid mostly at their ostiolar regions. After the liquid dries, a small crater at the top of the stromata is left. Cross sections of the stroma reveal the presence of one to several pycnidial locules which are well separated. A large number of unicellular, minute, hyaline, allantoid or gently curved conidia or pycniospores which measure 7×1.5 microns are found in these pycnidial locules and in the amber-colored liquid which oozes out from the locules.

b. GROWTH CHARACTERISTICS OF CYTOSPORA Sp. W.F.P.L. 13A

Cytospora sp. W.F.P.L. 13A can be grown successfully on a variety of media. The following growth characteristics were observed after incubation at ambient temperature (23°-24° C.) on various media for a period of four weeks.

(1). Malt-yeast extract agar (Malt extract, 1.0 g; yeast extract, 1.0 g; agar, 1.7 g; tap water*, 100 ml):

*tap water analysed to contain (milligrams/liter): bicarbonate 172, chloride 4, sulfate 11, silica 53.5, nitrate <5, calcium 35, magnesium 12, sodium 22, iron 0.24-5, manganese 0.05, fluoride 0.45, phosphate 0.09, zinc 0.0002–0.001, copper 0.002–0.003, mercury <0.0002 and cadmium <0.002

Excellent growth was observed. Moist yeast-like colonies were noted with concentric zones of hyaline mycelial growth causing ridges and furrows on the agar surface tangential to the advancing edge of the colonies. Mycelia which were moderately branched stuck to the agar surface when pulled. A large number of minute white to dark-brown stromata formed in rings on most mycelial colonies and some were totally buried in the agar. In this medium stromata appeared 7–10 days earlier than in other media tested and did not develop hair-like appendages on their out wall surfaces. No pigment was visible in the agar medium and no sporulating structures were observed other than pyciniospores produced inside the stromata.

(2). BBL Potato-dextrose Agar (PDA):

Excellent growth was observed with smooth, white to cream-colored younger mycelia developing in contrast to light-green to greenish-brown older portion of colonies. No pigment was visible in the agar medium and the colonies were dry. Stromata appeared after 3–5 weeks of growth; they varied in size and shape from half globose to spherical, and in color from dark-brown to black, and were glabrous or sometimes hirsute with multicellular appendages. Stromata were on the surface and within the agar. In general stromata appeared a week or two later than in malt-yeast extract agar and were larger in size, sometimes measuring almost a centimeter across.

(3). Tomato Juice Agar (20 ml Campbell's tomato juice with 80 ml of tap water, solidified with 1.7% agar):

Velvety-white dry mycelia were formed with a cream-colored underside. No pigments were produced. Only a few stromata were formed even after four weeks of growth.

(4). Gelatin (Gelatin, 3.0 g; glucose, 2.0 g; yeast extract, 1.0 g; tap water, 100 ml):

Abundant snow white dry mycelial growth was observed in the first two weeks. Later in the third and subsequent weeks, the mycelia became moist; liquefaction of gelation was noticeable only after 24–28 days of growth. There was no production of pigment either in the mycelia or in the medium. No sporulating bodies were formed.

(5). Sabouraud Liquid Medium+1.7%+1.5% Soluble Starch:

Excellent growth was observed with yeast-like, cream-colored mycelial colonies which grew both on the surface and into the agar. No pigment and no sporulating structures were formed. After three weeks of growth, Gram's iodine stain was used to detect the hydrolysis of starch. No residual starch could be detected within a 1-cm distance around the colony. This test indicates that the fungus hydrolyzes starch.

(6). Water Agar (Tap water 100 ml+1.7 g washed agar):

Very poor growth in the first week was observed. Later in the second and subsequent weeks elongated, thin, hyaline, sparingly branched hyphae covered the whole surface of the agar. Some hyphae measured 2–3 cm in length with no traces of pigmentation and remained hyaline throughout.

(7). Nutrient Agar (0.8% Difco Nutrient broth in 1.7% agar);

Very poor growth resulted. Mycelia were sparse, hyaline, and frequently in spirals or coils. No sporulating structures and no pigmentation were observed.

(8). Baoto Czapek Solution Agar;

Little or no growth resulted. In cases where growth was observed, sparse, hyaline extensively branched mycelia were formed. No sporulating structures were noticed.

(9). PDA with 1% Yeast Extract:

Excellent growth was noticed. External features of colonies resembled yeast-like growth. Mycelia grew both on the surface and into the medium and, when pulled, adhered to the agar. Surfaces of the agar showed ridges and furrows which may have been due to partial hydrolysis of the agar by this fungus. Older mycelia acquired dark green to brown pigmentation. No fruiting bodies were formed. Whereas the mycelia were dark green, little pigment diffused into the medium.

CARBON UTILIZATION

To determine which carbon source was suitable for the growth of the organism (and for the production of the antibiotic), Cytospora sp. W.F.P.L. 13A was grown at 25° C. in 50 ml of the basal medium [g/liter: $NH_4NO_3$, 1.0; $MGSO_4.7H_2O$, 0.7; $KH_2PO_4$, 0.9; $K_2HPO_4$, 0.7 yeast extract, (Difco) 0.1] with 1.5 percent of the test carbon source in each flask (Table 1). The initial pH of the medium was 6.0 to 6.2 before sterilizing and in general decreased during growth. Cultures were shaken at 115 rpm for four weeks (Table 1). During this period the growth characteristics of the fungus, the antibiotic activity against *Pseudomonas nigrifaciens* and the change in pH in each of the media were tested.

Excellent growth of mycelia (dry weight) was observed in those flasks containing glucose, mannose, maltose or fructose (Table 1). For these carbon sources the mycelial growth was observed 4–5 days prior to growth on the other carbon sources tested. In comparison to other carbon sources tested, antibiotic production was low.

The growth of the fungus was slower and the total amount of mycelial material produced (Table 1) was smaller when the fungus was grown on mannitol, lactose, sorbitol, arabinose or inositol. In contrast to the poorer vegetative growth on these carbon sources, there was, however, considerable antibiotic activity produced. In flasks containing mannitol the organism produced gray-colored mycelial balls with dark-brown to black globose stromata.

Various shades of yellow pigment diffused into the test media (Table 1) and also the mycelial material acquired different shades of dark-green to dark-brown pigments in some cases. There was no sporulating structures produced on most carbon sources tested.

TABLE 1

| \multicolumn{5}{c}{UTILIZATION OF CARBON SOURCE BY CYTOSPORA SP W.F.P.L. 13A} |
|---|---|---|---|---|
| Carbon Source | Dry Wt. of Mycelia | Terminal pH | Pigmentation | Antibiotic Activity* |
| Mannose | 253 mg | 2.45 | No pigment. | 0.40 mg |
| Maltose | 231.0 | 2.55 | light green | 0.240 |
| Fructose | 220.0 | 2.00 | light yellow | 2.00 |
| Glucose | 137.5 | 3.00 | light yellow | 2.00 |
| Xylose | 61.90 | 3.80 | no | 3.20 |
| Mannitol | 57.10 | 5.75 | no | 6.80 |
| Galactose | 26.00 | 4.40 | light yellow | 3.60 |
| Lactose | 23.50 | 5.90 | amber color | 20.00 |
| Glycerol | 23.00 | 6.45 | no pigment | 0.32 |
| Sorbitol | 20.00 | 5.50 | no pigment | 15.20 |
| Arabinose | 19.00 | 5.80 | crimson red | 6.00 |
| Sucrose | 15.00 | 6.45 | no pigment | 4.00 |
| Inositol | 11.00 | 6.20 | no pigment | 16.80 |
| Salicin | 7.50 | 3.80 | no pigment | 0.640 |

TABLE 1-continued

UTILIZATION OF CARBON SOURCE
BY CYTOSPORA SP W.F.P.L. 13A

| Carbon Source | Dry Wt. of Mycelia | Terminal pH | Pigmentation | Antibiotic Activity* |
|---|---|---|---|---|
| Rhamnose | 5.00 | 4.60 | no pigment | 4.80 |
| Control | 7.00 | 6.45 | no pigment | 0.060 |

*As in Example 3

Maintenance of Stock Cultures

Stock cultures of Cytospora sp. W.F.P.L. 13A can be maintained on PDA plates at 25° C. for a period of 4–6 weeks or can be stored on PDA slants at 4° C. for a period of 2–3 months. To keep the culture viable it is essential that the organism be periodically subcultured on the same medium. Addition of 1 percent yeast extract to the PDA medium helped to stimulate the organism to grow into the agar as well as on the surface of the agar; these types of slants can be stored at 4° C. for an extended period of time without losing much viability.

EXAMPLE 1

PRODUCTION AND PURIFICATION OF ANTIBIOTICS

The actively growing edges of a stock culture colony were used to inoculate 500 ml Erlenmeyer flasks containing 150–200 ml of sterile potato dextrose broth at a pH of 5.8 to 6.2.* Potato dextrose broth was prepared by homogenizing 60–70 grams potatoes in one liter of tap water followed by addition of 20 grams of glucose. Seed cultures of 200 ml were grown for a period of 4–7 days at 24° C. on a reciprocating shaker set at 115 rpm. Those seed cultures which showed high antimicrobial activity (as in Example 3) were inoculated into 10 liters of sterilized medium of the same composition. The aerobic growth was carried out at 26° C. with agitation at 350–400 rpm and with a supply fo 3–4 liters of sterile air per minute. As needed 500–100 μl sterile antifoam solution was added to the fermenter to keep the culture from foaming. Both the growth of the fungus and the antibiotic in the broth were monitored during the fermentation. The antibiotic activity of the broth was measured by using the paper-disc agar diffusion method on the susceptible organism Pseudomonas nigrifaciens (as described in Example 3). This organism is a halophilic and foul-smelling bacterium commonly found in salt-water lakes and bays.

*analyzed as containing (grams/10 liters): ammonium sulfate 0.15, magnesium chloride 0.0075, magnesium chloride 0.0225, potassium phosphate (monobasic) 0.355, ferrous sulfate 0.00192, manganous sulfate 0.00018, zinc chloride 0.00002 and copper sulfate 0.000007.

During the first thirty hours of fermentation only a small amount of new mycelial material was produced. A loose cottony mesh of new mycelia became visible around 36–40 hrs. of fermentation. Only a small amount of antibiotic was present in the broth for the first 24–40 hrs. of growth. About eighty percent of total hyphal material and the antibiotic was formed during the period beginning the third day of fermentation (36–40 hrs.) to the end of the fifth day. Beyond the sixth day until to the end of the ninth day, the vegetative growth was considerably slowed, and the antibiotic activity in the medium increased to a maximum concentration around the ninth day. Prolonging the fermentation beyond the ninth day did not significantly increase the antibiotic yield (FIG. 1). Usually a growth duration of 8–10 days was sufficient for an optimum yield of the antibiotic.

For maximum antibiotic production, the potato broth containing 2% glucose proved to be the medium of choice. Aeration was absolutely essential for the production of the antibiotic but was not necessary for the growth of the fungus. The donor fungus grew equally well under anaerobic conditions.

During aerobic growth the pH of the medium gradually decreased from 6.2 to 5.0 around the fifth day to pH 4.5 at around the ninth day. The mycelia were light-cream to white in color during the first 72–96 hrs. of growth and turned green to dark-green at around seven days. No pigment was observed in the medium for the first 4–5 days of growth, but after the fifth day, a light-green pigment diffused into the medium. No sporulating structures were produced during the entire 9–11 days of growth; the organism multiplied only by the propagation of the vegetative mycelia.

A high level of antibiotic activity was observed both in mycelia and in the cell-free liquid portion of the fermentation culture. Thus, for an efficient extraction of the antibiotic it was desirable to separate the mycelia from the broth. This was easily done (i) by a gravity filtration of the broth through a double layer of cheese cloth, or (ii) by centrifugation with a continuous-flow centrifuge, or (iii) by simply keeping the fermenter culture overnight at 5°–10° C. without aeration to allow the cells to settle to the bottom of the container; the top clear liquid could then be easily decanted. Typical growth in 10–12 liters yielded around 900–1500 grams (fresh weight) of mycelial material.

The antibiotic was extracted from the cultures and purified as follows:

The cell-free filtrate was extracted twice, each time with 2 liters of chloroform. After the removal of the relatively inactive aqueous layer, the active chloroform layers were combined, pooled with the chloroform extract of mycelia (next paragraph), filtered, and concentrated under reduced pressure. (Other solvents suitable for the extraction of the antibiotic from the cultures were ethyl acetate, methylene chloride, ethylene chloride, methyl ethyl ketone, methyl isobutyl ketone, butyl alcohol or butyl chloride.) The residue which was a greenish-yellow, viscous liquid was triturated with 300–400 ml of petroleum ether (bp: 60°–100° C.) to extract fat-soluble impurities and some antibiotic activity which was processed separately. The petroleum ether-insoluble material which was a greenish-amber amorphous substance was triturated with 150–200 ml of anhydrous diethyl ether or 70–80 ml of methylene chloride, the extract filtered through a sintered-glass filter, and the volume reduced to 50–60 ml under reduced pressure. The concentrated ether or methylene chloride solution was added dropwise to 20-volumes of petroleum ether (bp: 60°–110° C.) at 25° C. while mixing with a magnetic stirrer. The light-yellow to white-colored antibiotic precipitate was collected on a sintered-glass filter and washed 3–4 times with additional small portions of petroleum ether. Other suitable solvent combinations for the extraction and precipitation of the antibiotic from the culture filtrate are: (a) methylene chloride followed by petroleum ether or heptane (1:20 in each case); (b) methylene chloride, followed by petroleum ether or heptane (1:20, in each case); (c) methyl ethyl ketone followed by petroleum ether (1:20); (d) absolute ethanol followed by petroleum ether (1:20) or (e) diisopropyl ether followed by petroleum ether (1:20). Alternatively, various combinations and ratios of the above extracting and precipitating agents can be used to recover the antibiotic.

The aforementioned residual mycelial material (900–1500 grams fresh weight) was processed separately by homogenizing in the presence of acetone with a mortar and pestle. Addition of glass beads or any other abrasive material helped to disrupt cells. The homogenate was filtered, the filtrate concentrated under reduced pressure and the residue triturated with 200–300 ml chloroform. This latter chloroform extract was pooled with the chloroform extract of the filtrate for further processing of the antibiotic.

The yield of antibiotic varied from batch to batch. For each 20–24 liters of fermentation culture, 10–12 grams of crude antibiotic material was obtained as a light-yellow to amber-colored, partially crystalline solid. The antibiotic material was further purified by 2"×15" column chromatography on silica gel 60–200 mesh (Baker Analyzed Reagent). A material, hereinafter referred to as Grahamimycin A, was eluted with one liter of 2% ether in methylene dichloride. Another fraction, hereinafter referred to as Grahamimycin B complex, which is more polar than Grahamimycin A, was eluted from the column with 500 ml of 10% ether in methylene chloride. A third active fraction (hereinafter referred to as Grahamimycin C) was eluted with 200 ml methanol. The fractionation scheme described is summarized in FIG. 2. Various fractions which have antibiotic activity against both $Ps.$ $nigrifaciens$ and $Bacillus$ $subtilis$ are noted. The Grahamimycin A fraction was again subjected to column chromatography employing a 5.4×50 cm on silica gel (E. Merck PF 254) employing 20% ether in dichloromethane at a rate of 24 ml per minute. 30–70 ml fractions were collected. Fractions 31–41 were obtained employing 36% ether in dichloromethane. Elution was then continued employing 50% ether in dichloromethane. Fractions 42–49 were evaporated, and the resultant solid crystallized from methylene dichloride with hexane added to first crystal at boiling. Grahamimycin A was crystallized from 95% ethanol 4–6 times, and then from methylene chloride-diisopropyl ether to afford pure antibiotic.

EXAMPLE 2

CHARACTERIZATION AND IDENTIFICATION OF GRAHAMIMYCIN A (1). Appearance

The pure Grahamimycin A is a white to light-yellow, semi-transparent crystalline compound. The color, size and shape of the crystals formed were dependent on the solvents and conditions used for crystallization. Flat disc-shaped crystals aggregated into various structures resembling branched bundles of crystals when 1:1 ethyl ether and petroleum ether had been used. From methanol and petroleum ether, rhomboidal crystals were formed; needle-shaped crystals were formed when ethyl acetate and petroleum ether had been used. Thin, semi-transparent plate-like crystals were formed from methylene chloride-hexane, methylene chloride-diisopropyl or ethanol.

(2). Melting Point

Melting point determinations were carried out in sealed evacuated glass capillaries using a Thomas-Hoover Unimelt apparatus. Extensive decomposition occurred as evidenced by the formation of an intensely yellow melt, although considerable biological activity remained in the fused material. The range of melting was variable, but occurred between 140°–148° C.

(3). Elemental Composition

Elemental analysis was performed by Galbraith Laboratories and gave 59.46% C and 6.66% H, with less than 0.1% N. This agrees with a calculated formula of $C_{14}H_{18}O_6$ (59.57% C, 6.38 H).

(4). Optical Rotation

The optical rotation was determined at two separate concentrations in chloroform and the specific rotation found to be $[\alpha]_D^{22} - 34°$ (1.47 in $CHCl_3$).

(5). Molecular Weight Determinations

The molecular weight of Grahamimycin A was determined by direct injection using both electron-impact and chemical-ionization modes for mass spectroscopy. The former method showed $M^+$ (molecular ion) to be 282 amu, and the latter showed $(M+1)^+$ to be 283 amu. A similar determination employing GC-MS (combined gas chromatography-mass spectroscopy) on a trimethylsilyl derivative, prepared by heating the antibiotic briefly (80° C. for 20 min.) in bis-trimethylsilylacetamide, showed $M^+$ at 356. Two minor components from the silylation mixture also showed a similar molecular ion. When the antibiotic which had been dissolved in ethyl acetate was injected into GLC no response and therefore no mass spectrum was obtained. However, the same compound after silylation with bis-trimethylsilylacetamide for 20 minutes at 80° C. gave a good response on GLC (4 ft.×⅛ inch SP 400 at 180°–280° C.; programmed at 6° C./minute). A single major peak accounting for 95% of the area under all peaks and two to three minor peaks were observed. The electron-impact mass spectrum of this TMS-derivative of the antibiotic showed a molecular ion at 356 and a major fragment ion at 143.

(6). UV and Visible Spectra

A continuous end absorption with a shoulder at 243 nm and a maximum at 353 nm was observed (FIG. 3). No absorption maxima were observed in the visible region of the spectrum.

(7). The Infrared Absorption Maxima

Figure 4:
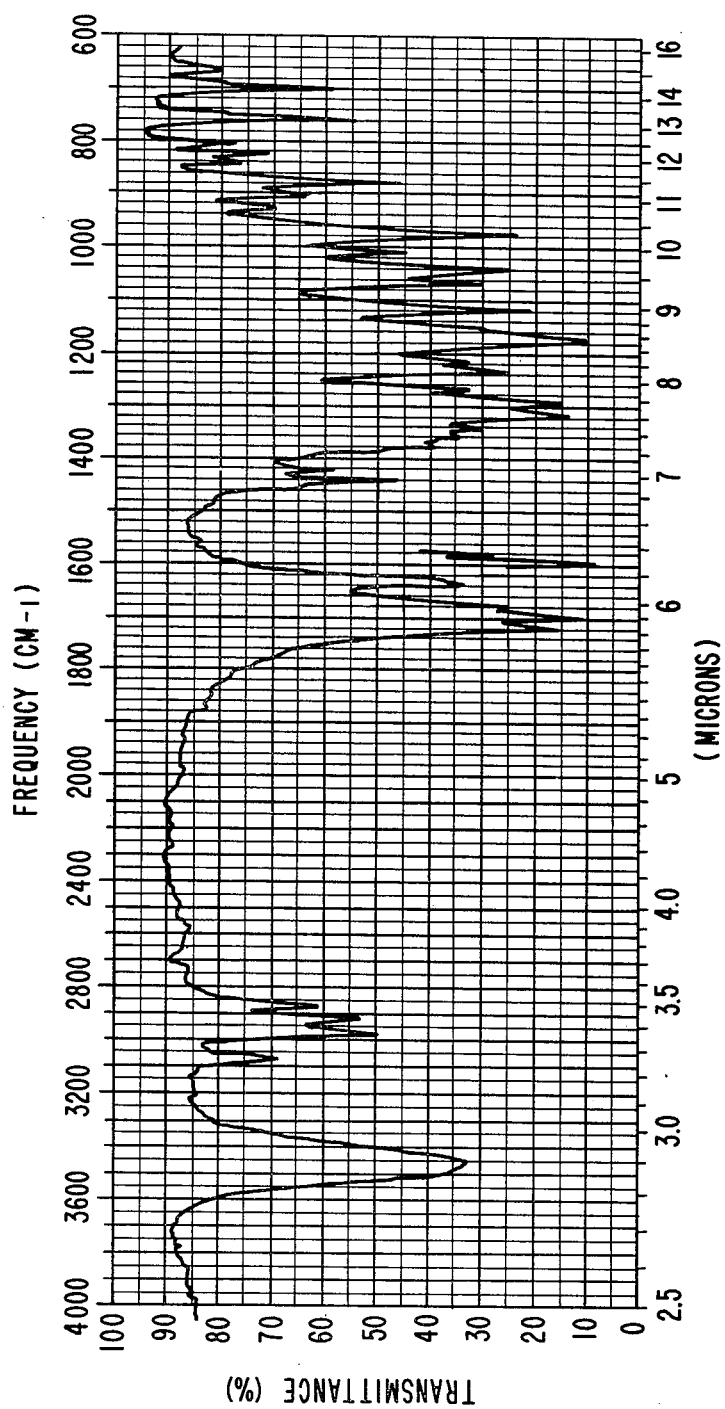

The infrared absorption spectrum of Grahamimycin A was obtained in a potassium bromide pellet using a Perkin-Elmer infrared spectrophotometer model 700. This spectrum is shown in FIG. 4. Referring to FIG. 4 the antibiotic shows strong absorption bands at the following positions, expressed in $cm^{-1}$: 657, 699, 746, 753, 813, 832, 834, 895, 909, 935, 976, 1020, 1040, 1070, 1115, 1152, 1176, 1220, 1235, 1267, 1299, 1316, 1346, 1381, 1420, 1447, 1468, 1616, 1698, 1724, 2898.5, 2933, 2994, 3086, 3460.

(8) Proton Magnetic Resonance Spectra of the Grahamimycin A in $CDCl_3$

Spectra were obtained on a Varian Associates Model EM360 at 60 MHz and on a JEOL Model MH100 at 100 MHz.

| Chemical Shift, δ | # of Protons | Pattern | Possible Assignment |
|---|---|---|---|
| 1.38 | 3H | doublet | methyl |
| 1.43 | 3H | doublet | methyl |
| 2.30 | 2H | several multiplets | |
| 4.18 | 1H | doublet | alcohol OH (disappears upon deuteration) |
| 4.50 | 1H | multiplet | H—C—OH |
| 5.20 | 2H | two multiplets | |
| 5.80 | 1H | doublet (part of AB) | olefinic proton |

-continued

| Chemical Shift, δ | # of Protons | Pattern | Possible Assignment |
|---|---|---|---|
| 6.70 | 1H | doublet (part of AB) | olefinic proton |
| 6.72 | 1H | multiplet (part of AB split) | olefinic proton |
| 7.12 | 1H | doublet (part of AB) | Olefinic proton |

Decoupling Experiment

| Irradiation frequency, δ | Results |
|---|---|
| 1. 1.38–1.43 | 5.20 altered |
| 2. 5.20 | Doublets at 1.38 and 1.43 go to 2 singlets; alterations at 2.14 |
| 3. 5.80 | Multiplet at 6.72 is altered |
| 4. 2.30 | Multiplet at 6.72 goes to doublet and some change at 5.20 |

(9). Carbon-13 Magnetic Resonance Spectra of Antibiotic in $CDCl_3$

Spectra were obtained on a Brucker WH-90 instrument at 90 MHZ.

Proton Decoupled, Chemical Shifts from TMS External Standard

| Chemical shift, δ | Assignment |
|---|---|
| 18.9 | Methyl carbon |
| 20.0 | Methyl carbon |
| 40.2 | Two methylene carbons |
| 66.3 | Carbon bonded to oxygen by single bond |
| 70.5 | Carbon bonded to oxygen by single bond |
| 73.0 | Carbon bonded to oxygen by single bond |
| 126.8 | Olefinic carbon |
| 131.9 | Olefinic carbon |
| 135.2 | Olefinic carbon |
| 143.4 | Olefinic carbon |
| 165.3 | Carbonyl carbon of ester |
| 166.0 | Carbonyl carbon of ester |
| 201.4 | Carbonyl carbon of ketone |

(10). Comments on the NMR

The uncoupled spectra are consistent with assignments. No protons are seen with any carbonyl assignments. Each olefinic carbon has one directly bonded proton. Methyl carbons appear as quartets in undecoupled spectra. The three carbons each bonded to oxygen by a single bond represent the two carbons of each of two alcohols in two ester linkages and one carbon of a secondary alcohol. All carbon spectra of these three are doublets in undecoupled spectra showing that only one proton is bonded to each of these three carbons. In $CDCl_3$ the two methylene carbons appear as a single line. In $CD_3OD$ two resonances are observed but only 0.1 ppm apart. The undecoupled spectra in $CDCl_3$ reveals a triplet showing that two protons are directly bonded to each of the two carbons.

(11). Stability of Grahamimycin A

Crystalline Grahamimycin A retained most of its biological activity after melting into an amber-colored liquid and further heating up to 150° C. for 2–3 minutes. When heated in ethanolic solutions (2 mg/ml) inside evacuated and sealed ampules at 100° C. for 1 hr., 70% of the activity was lost. More than 90% of the activity was lost after heating at 100° C. for 2 hours and no activity was detectable after 3 hours. When dissolved in chloroform for extended periods at 23° C. some decomposition to a yellow oily material took place although there was no significant loss in biological activity of the antibiotic.

The silylated derivatives of the molecule lost more than 80% of the activity. Reaction with diazomethane or transesterification in $BF_3$-methanol resulted in complete loss of antibiotic activity. Acetylation in acetic anhydridepyridine resulted in complete retention of biological activity. Tetrahydro Grahamimycin A prepared by hydrogenation as hereinafter described was not active.

(12). Solubility

Grahamimycin A is soluble at 23° C. in methanol, ethanol, propanol, butanol, methylene chloride, ethylene chloride, chloroform, butylchloride, acetone, methylethyl ketone, methylisobutyl ketone, ethylacetate, acetonitrile, diethylether, and diisopropyl ether. It is sparingly soluble in water and carbon tetrachloride, and almost insoluble in petroleum ether, heptane and hexane.

(13). Color Reactions

Grahamimycin A gave negative tests with anthrone, phenol-sulfuric acid and ninhydrin.

(14). Chromatrographic Migration

Grahamimycin A gave a single symmetrical spot when tested by using Kodak-plastic ready-made chromotographic migration silica gel plates with different solvent systems. The antibiotic spot on thin layer chromatography (TLC) was observed under UV because of its fluorescence; the biological activity of the antibiotic on TLC was determined by running a bioautogram of plates with P. nigrifacines as a susceptible organism. In all these chromatograms the biological activity was associated with the UV-fluorescent spot on the chromatogram.

Grahamimycin A is the macrocyclic dilactone corresponding to the structural formula:

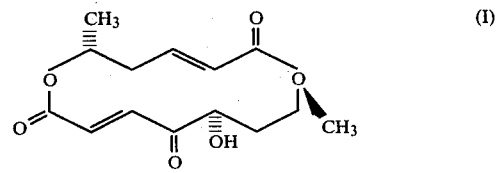

(I)

The chemical structure of Grahamimycin A was established by a combination of chemical and spectral methods. The composition data obtained from combustion analysis and mass spectroscopy coupled with structural assignments from both pmr and cmr studies indicated the presence of only one ring. The pmr and cmr decoupling experiments strongly indicated the presence of an α-ketol function which was confirmed by selective cleavage of this function with periodic acid to form a single carboxyaldehyde. The tetrahydro form of the antibiotic was similarly cleaved to a carboxyaldehyde in which it was possible to discern a succinate moiety. This confirmed the assignment of a

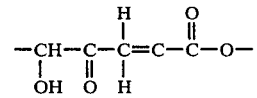

substructure indicated by the nmr experiments.

From these data and the optical rotation the structure was shown to be 12-hydroxy-6,14-dimethyl-1,7-dioxacyclotetradeca-3,9-diene-2,8-11-trione [3E, 6R, 9E, 12R, 14S].

A similar dilactone has been reported in the literature (J. MacMillan and T. Simpson, *JCS Perkin* 1,14, 1487 (1973)) which is designed colletoketol (12-hydroxy-6,14-dimethyl-1,7-dioxyacyclotetradeca-3,9-diene-2,8-11-trione[3E, 6R, 9E, 12R, 14R]). However, comparison of the i.r. spectra of Grahamimycin A and colletoketol, as well as the melting points and mixed melting points of the corresponding tetrahydro derivatives established that these substances, although very similar, were not identical. Tetrahydro-Grahamimycin A was prepared by hydrogenating 130 mg of Grahamimycin A in 5 ml absolute alcohol over 1.1 mg Adam's Catalyst for 1 hour. The crude material after evaporation of the ethanol was chromatographed on a 12×1 cm column of Silica Gel eluted with 20% $Et_2O$-$CH_2Cl_2$. Recrystallization from $CH_2Cl_2$-$Et_2O$ afforded plates mp 103°–105° C.

The relative and absolute stereochemistry of Grahamimycin A was established as follows. From the fermentation mixture a related substance Grahamimycin B was isolated as above. Spectral evidence suggested that Grahamimycin B was a hydroxy-derivative related to Grahamimycin A by addition of the elements of water across the C-9-C-10 double bond. This was confirmed by conversion of Grahamimycin A and B to the same tetrahydroacetate by treatment first with acetic anhydride in pyridine followed by hydrogenation over platinum in the following manner. A 62.6 mg sample of Grahamimycin A was dissolved in 0.5 ml of dry pyridine. To this solution was added 0.2 ml acetic anhydride. After 1½ hours at room temperature the excess reagents were evaporated at reduced pressure. The residue was chromatographed on a ½×20 inch column of Woelm 32–63μ Silica Gel eluted with a mixture of 20% $Et_2O$-80% $CH_2Cl_2$ to afford 47 mg of acetate as a pale yellow oil. All attempts to crystallize the acetate failed.

Reduction of a 37 mg sample of Grahamimycin A acetate with excess $H_2$ in 1 ml absolute ethanol over 1.0 mg of Adam's catalyst afforded, after evaporation of the solvent at reduced pressure and preparative thin-layer chromatography on Silica Gel (E. Merck $PF_{254}$) developed with 20% $Et_2O$-$CH_2Cl_2$, 10 mg of crystalline tetrahydroacetate mp 107°–8°.

In a like manner, a 48.7 mg sample of Grahamimycin B was treated with 0.5 ml pyridine and 0.25 ml acetic anhydride. After stirring overnight at room temperature the reaction mixture was poured into water and extracted three times with ether. The combined ether extracts were washed with 10% aqueous acetic acid. After drying with anhydrous magnesium sulfate the extract was concentrated to a yellow oil at reduced pressure.

The crude material was filtered through a 0.5×10 cm Silica Gel column, then chromatographed on a Silica Gel preparative plate developed with 5% $Et_2O$-$CH_2Cl_2$ to afford 34 mg of a pale yellow oil which appeared to be identical to Grahamimycin acetate. The acetic anhydride-pyridine reagent apparently causes elimination of the C-9 hydroxyl with formation of the C-9-C-10 double bond.

The identity of the acetates from Grahamimycins A and B was confirmed by hydrogenation of the acetate from Grahamimycin B, by the aforementioned hydrogenation procedure, to a crystalline substance mp 106°–7° which did not cause depression of the melting point upon admixture with tetrahydro-Grahamimycin A acetate. This establishes that Grahamimycins A and B have the same ring structures and stereochemistry.

An X-ray structure of the highly crystalline Grahamimycin B afforded confirmation of the structures proposed for Grahamimycin B and Grahamimycin A and also provided the relative stereochemistry. The absolute configuration was established by mild basic hydrolysis which resulted in the formation of 5(R)-hydroxy-2(E)-hexenoic acid $[\alpha]_D^{23}$−11.7° (lit. $[\alpha]_D^{23}$−10°). Since the C-5 asymmetric center of the hydroxyhexenoic acid is the C-2 center of Grahamimycins A and B the C-2 center must have the R configuration. Therefore, the absolute configuration of Grahamimycin B is that shown in structure (II) and Grahamimycin A in structure (I).

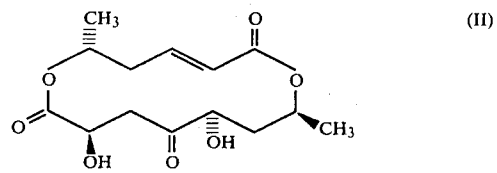

(II)

EXAMPLE 3

ANTIMICROBIAL SPECTRUM OF THE GRAHAMIMYCIN A

Turbidimetric, tube dilution, and petri-dish zonal-inhibition techniques were employed to evaluate the antimicrobial efficacy of the Grahamimycins. Since Grahamimycin A was only slightly soluble in water, it was dissolved first in small amounts of methanol or ethanol to make standard solutions. For control samples in the assays, organic solvent was added to compensate for any inhibitory effect due to the solvent. Most of the inhibition studies were performed by using a modified paper-disc zonal-inhibition technique in which a known amount of stock solution of the antibiotic was dispensed on paper discs on a nylon support. The discs were transferred, after the removal of the solvents by air evaporation for two hours, onto the surface of seeded agar containing a uniform dispersion of the test organism prepared as described in the following paragraph. To ensure reproducible diffusion of the antibiotic, discs were incubated for a fixed time (at least six hours) at 2° C. prior to growth of the test organism at 37° C.

In order to seed the agar plates or to inoculate liquid media for turbidimetric measurements test organisms which had been grown overnight or to log phase were used. Different types of suitable media were employed to grow more fastidious types of microorganisms. In most tests nutrient broth was used. After overnight growth, 6–10 ml of the bacterial culture was added while mixing to 450–500 ml of sterile nutrient agar in a temperature range of 40°–45° C. Ten-milliliter aliquots of this bacterial suspension were dispensed into each 100 mm petri dish. Most of these seeded agar plates were used on the same day but they could be stored at 2°–4° C. for 5–6 days without affecting their response to the antibiotic.

Results are summarized in Table 2. As evident, Grahamimycin A is broad spectrum antibiotic that is active against gram-positive and gram-negative bacteria, cyanobacteria (blue-green algae), green algae and fungi. A semilogarithmic plot of inhibition zone width for *Ps. nigrifaciens* versus antibiotic dosage reveals linearity as would be expected.

TABLE 2

ANTIMICROBIAL SPECTRUM OF GRAHAMIMYCIN-A

| Organisms | Inhibition Zone Width (cm) for Antibiotic Applied (μg/disc) | | | | | | |
|---|---|---|---|---|---|---|---|
| | 2 μg | 5 μg | 10 μg | 15 μg | 20 μg | 30 μg | 40 μg |
| BACTERIA | | | | | | | |
| *Alcaligenes faecalis* | —[a] | 1.40 | 1.70 | 1.70 | 1.70 | 2.20 | 2.20 |
| *Arthrobacter globiniformis* | 1.70 | 1.975 | 2.05 | 2.40 | 2.75 | 3.10 | 3.50 |
| *Bacillus cereus* | 1.40 | 1.90 | 2.30 | 1.50 | 2.70 | 3.20 | 3.20 |
| *Bacillus lactosporus* | 1.90 | 2.40 | 2.80 | 2.90 | 3.10 | 3.40 | 3.50 |
| *Bacillus megatherium* | 1.70 | 2.10 | 2.80 | 3.10 | 3.40 | 3.55 | 3.80 |
| *Bacillus subtilis* | 1.95 | 2.55 | 3.10 | 3.20 | 3.30 | 3.55 | 3.80 |
| *Bacillus thuringensis* | 1.70 | 2.25 | 2.55 | 2.75 | 2.95 | 3.35 | 3.40 |
| Citrobacter sp. | — | — | — | — | — | — | 1.90 |
| *Corynebacterium diphtheriae* | — | ±[b] | +[c] | + | + | + | + |
| *Corynebacterium ulcereus* | 1.90 | 2.50 | 2.70 | 2.95 | 3.20 | 3.50 | 3.50 |
| *Edwardsiella* sp. | 1.40 | 1.70 | 1.90 | 2.15 | 2.20 | 2.20 | 2.50 |
| *Enterobacter aerogenes* | — | — | — | — | — | 2.50 | 2.50 |
| *Erwinia amylovorous* | 1.50 | 1.60 | 1.85 | 2.15 | 2.50 | 2.60 | 2.85 |
| *Escherichia coli* | — | ± | ± | 1.55 | 1.60 | 1.65 | 1.80 |
| *Herella vaginicola* | — | — | 1.60 | 1.70 | 1.85 | 2.25 | 2.30 |
| *Klebsiella* sp. | — | — | — | — | 1.50 | 1.50 | 1.50 |
| *Micrococcus amylovorous* | 1.45 | 1.55 | 1.65 | 1.80 | 2.15 | 2.44 | 2.70 |
| *Micrococcus* sp. | — | 1.70 | 1.80 | 2.05 | 2.00 | 2.20 | 2.60 |
| *Proteus vulgaris* | — | — | — | — | — | — | — |
| *Pseudomonas aeruginosa* | — | + | + | + | + | + | + |
| *Pseudomonas nigrifaciens* | 1.55 | 1.70 | 2.30 | 2.35 | 2.50 | 2.60 | 2.90 |
| *Pseudomonas stutzeri* | — | — | 1.50 | 1.55 | 1.63 | 1.70 | 2.10 |
| *Salmonella anatum* | — | — | — | — | — | — | — |
| *Salmonella monteroides* | — | — | — | ± | 1.55 | 1.60 | 1.70 |
| *Salmonella typhi* | — | — | — | — | 1.50 | 1.50 | 1.50 |
| *Salmonella typhimurium* | 1.50 | 1.95 | 2.0 | 2.15 | 2.20 | 2.40 | 2.60 |
| *Salmonella worthington* | — | — | 1.50 | 1.60 | 1.80 | 1.80 | 1.85 |
| *Sarcina lutea* | + | + | + | + | + | + | + |
| *Serratia marcescens* | 1.40 | 1.90 | 1.95 | 2.00 | 2.10 | 2.30 | 2.30 |
| *Shigella flexneri* | 1.45 | 1.90 | 2.30 | 2.30 | 2.30 | 2.30 | 2.30 |
| *Shigella sonnei* | — | — | — | — | — | — | — |
| *Shigella boydii* | — | — | 1.55 | 1.80 | 1.85 | 1.90 | 2.23 |
| *Staphylococcus aureus* | 1.45 | 1.55 | 1.90 | 2.15 | 2.25 | 2.55 | 2.85 |
| *Staphylococcus epidermides* | — | — | — | 1.45 | 1.70 | 1.80 | 1.95 |
| *Streptococcus faecalis* | — | — | + | + | + | + | + |
| *Streptococcus lactis* | 1.45 | 1.90 | 2.30 | 2.30 | 2.30 | 2.80 | 2.80 |
| BLUE GREEN ALGAE | | | | | | | |
| *Anabaena cylindrica* | 3.3 | 3.5 | 4.0 | 4.2 | 4.50 | 6.0 | 7.0 |
| *Fischerella musicola* | + | + | + | + | + | + | + |
| *Lingbya* sp. | 1.70 | 2.20 | 3.2 | 3.80 | 4.50 | 5.00 | 6.0> |
| *Oscillatoria chalybea* | 2.20 | 2.90 | 3.20 | 3.50 | 3.80 | 5.00 | 5.5> |
| *Oscillatoria formosa* | 2.00 | 2.50 | 2.70 | 3.60 | 4.50 | 4.8–5.00 | 5.0–6.00> |
| *Oscillatoria tenuis* | 2.50 | 3.50 | 3.50 | 4.00 | 4.00 | 5.0> | 5.0> |
| *Plectonema boryalis* | 1.90 | 3.50 | 4.20 | 4.35 | 4.50 | 5.00 | 6.00 |
| *Synecococcus cedrorum* | 1.90 | 3.50 | 5.00 | 5.20 | 5.50 | 6.00 | 7.00 |
| GREEN ALGAE | | | | | | | |
| *Chlamydomonas moewusii* | — | — | — | 1.45 | 1.60 | 1.60 | 1.60 |
| *Pandorina morum* | 1.40 | 1.60 | 2.00 | 2.25 | 2.40 | 2.60 | |
| FUNGI | | | | | | | |
| *Ascoidea rubescens* | — | — | + | + | + | + | + |
| *Candida albicans* | — | — | — | ± | + | + | + |
| *Coniophora puteana* | — | — | — | — | — | — | — |
| *Corticum galactum* | — | — | — | — | — | — | — |
| *Cytospora decipiens* | — | — | — | — | — | — | — |
| *Cytospora* sp. W.F.P.L. | — | — | — | — | — | — | — |
| *Dipodascus uninucleatus* | — | — | + | + | + | + | + |
| *Glomerella cingulate* | + | + | + | + | + | + | + |
| *Odontia bicolor* | — | — | — | — | — | — | — |
| *Saccharomyces kluyeuri* | — | — | ± | + | + | + | + |
| *Sclerotium cepivorum* | — | — | — | — | — | — | — |
| *Sclerotium rolfeii* | — | — | — | — | — | — | — |
| *Trametus cerealis* | — | — | — | — | — | — | — |
| *Trechispora* sp. | — | — | — | — | — | — | — |

[a] not inhibited —
[b] partially inhibited ±
[c] inhibited +

EXAMPLE 4

TOXICITY OF GRAMIMYCIN A-C COMPLEX

Intraperitonial injections of 100 mg of crude Grahamimycin A-C complex (see FIG. 2) per Kg body weight of adult mice did not induce any toxic symptoms. Similarly 300 mg/Kg body weight of an oral dose did not produce any toxic symptoms.

EXAMPLE 5

GRAHAMIMYCIN B AND CONVERSION TO GRAHAMIMYCIN A AND GRAHAMIMYCIN A ACETATE 4.23 grams of crude light yellow to amber-colored partially crystalline solid antibiotic material obtained in Example 1 (FIG. 2—crude Grahamimycin A, B, C, Complex) was placed on a 1"×6" silica gel column (Baker Analysed Reagent) and consecutively eluted with the following solvents.

| Fraction | Solvent | Weight and Composition of isolated solids |
|---|---|---|
| 1 | 200 ml 2% ether in methylene chloride | 2.621g-mostly Grahamimycin A |
| 2 | 200 ml 2% ether in methylene chloride | 0.214g-mostly Grahamimycin B |
| 3 | 100 ml 10% ether in methylene chloride | 0.063g-mostly Grahamimycin B |
| 4 | 100 ml 10% ether in methylene chloride | 0.09g-mostly Grahamimycin B |
| 5 | 100 ml methanol | 1.25-mostly Grahamimycin C |

The solids from fractions 2, 3 and 4 were combined (0.363 grams) and placed on a 2.5×49 cm. silica gel column Merck Silica 60 (40-60 microno) and eluted with 5% methanol-20% ether in methylene chloride at 24 ml/minute to obtain 30-70 ml tubes which yielded three fractions, a complex mixture (TLC, $R_f 0.6$) (tube 4); a second three component complex mixture (TLC, $R_f 0.5$) (tubes 5-7); and Grahamimycin B (tubes 8-11). The Grahamimycin B fraction isolated by evaporation (104 mg) was recrystallized four times from methanol, then 50% methylene chloride, 50% ether-hexane to yield 50 mg of Grahamimycin B mp 125°-126° C.

A 10.3 mg sample of the above Grahamimycin B was dissolved in 0.25 ml of pyridine and treated with 0.1 ml of acetic anhydride. TLC on silica gel (10% ether in methylene chloride) showed the reaction product to be a mixture of Grahamimycin A and the acetate of Grahamimycin A.

EXAMPLE 6

GRAHAMIMYCIN A STEARATE.

A 34 mg sample of Grahamimycin A was dissolved in 0.25 ml pyridine. Stearoyl chloride (Eastman), 100 μl, was added with stirring. After 4 hours at room temperature the mixture was poured in 5% aqueous $H_2SO_4$ overlaid with ether. The layers were separated and the ether layer was washed sequentially with 5% $H_2SO_4$, $H_2O$, and brine, then dried with anhydrous $MgSO_4$ and concentrated at reduced pressure to afford a yellow oil.

The crude product was chromatographed on a silica gel preparative plate developed with 3% ether in dichloromethane. The band at $R_f 0.6$ was removed and extracted to afford 38 mg (58%) of Grahamimycin A stearate as a clear, colorless oil. Upon cooling this material forms a waxy solid.

As can be seen from the previously described Grahamimycin A acetate and the preceding example, esters of Grahamimycin A can be formed, which esters are biologically active. These esters are also hydrolyzable to provide Grahamimycin A at a desired rate. Grahamimycin A esters can be formed by conventional esterification techniques where a free carboxyl group or an acid halide group is reacted with the hydroxyl group with the aid of known dehydrating or dehydrohalogenating agents. The ester group can be derived from saturated or unsaturated, straight or branched, substituted or unsubstituted aliphatic acids containing 1 to about 20 and preferably 2 to about 10 carbon atoms. Suitable acids include RCOOH were R is methyl, ethyl, propyl, isopropyl, tert butyl amyl, isoamyl, hexyl, heptyl and octyl, maleic acid, malonic acid, succinic acid, stearic acid, glutaric acid, cyclohexane carboxylic acid and substituted or unsubstituted benzoic acid. Preferably the acid is a pharaceutically acceptable acid.

EXAMPLE 7

The broad antimicrobial nature of Grahamimycin A makes it an excellent substance for use on a variety of microbially induced mammalian disorders, including its possible use as a topical ointment in healing of skin wounds. In the following study, the efficiency in healing of infected skin wounds in laboratory animals is set forth:

Two sets of five mice each were used for this study. The back portions of each mouse were shaved to facilitate the application of the antibiotic solution to the infected wounds. On the skin of each mouse, three to four longitudinal incisions ranging from 1.5 to 2.0 mm deep and 10 to 15 mm in length were made. A drop of log-phase (approximately $10^6$ organisms per ml) pathogenic *Staphyloccocus aureus* was smeared on the surface of the wounds with a cotton swab. After 30 to 45 minutes, the wounds in one set of animals were swabbed with a drop of 2 mg/ml aqueous solution of Grahamimycin A. The mice were caged and given food and water ad libitum.

General morphological changes in wounds were recorded. For the antomical study, the skin sections of mice around the incision areas were excised and preserved in FAA. Permanent slides from microtome sections of skin were also prepared to serve any abnormalities in the healed wounds.

Those wounds on mice which were not treated by the antibiotic solution become reddened, raised, crested, cankerous and showed all symptoms of inflammation and infection. All of the treated wounds healed with little reddening and in some mice the healing was so perfect that it was difficult to locate the original incision scar. Anatomical details did not reveal any abnormalities of accumulation of oil or fat in the treated samples and skin sections were almost identical to the unwounded areas of the skin.

EXAMPLE 8

Grahamimycin A was shown effective against *Neisseria gonorrhea* strain 2686, colony 4, grown at 37° C. in liquid culture where the medium was GC medium base (Difco) supplemented as described in Gilbs et al *J. Exp. Med.* 141, 155 (1975). At 10 μg/ml Grahamimycin A was effective (no growth); at 1 μg/ml there was only a slight, if any, inhibitory effect.

*Cytospora sp.* W.F.P.L. 13A has been deposited with the American Type Culture Collection in accordance with In re Argoudelis et al, 168 U.S.P.Q. 99 as ATCC 20502.

We claim:

1. A macrocyclic polylactone corresponding to the formula:

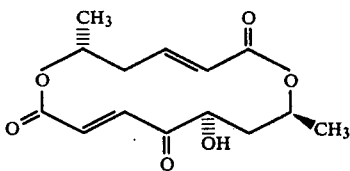

and pharmacalogically acceptable esters thereof.

2. The compound, as in claim 1, Grahamimycin A which
  (a) is a white to light yellow, semitransparent crystalline compound, the color, size and shape of the crystals being dependent on the solvents and conditions used for crystallization;
  (b) has a melting point 140°–148° C. (dec);
  (c) has a molecular formula $C_{14}H_{18}O_6$;
  (d) has an elemental analysis in substantially the following proportions: 59.46% C. and 6.66% H, with less than 0.1% N;
  (e) has specic rotation of $[\alpha]_D^{22} -34°$ (1.47 in $CHCl_3$);
  (f) has an infrared spectrum as shown in accompanying FIG. 4;
  (g) has the structural formula

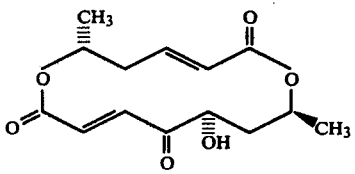

3. The acetate ester of the compound of claim 2.

4. A macrocyclic polylactone corresponding to the formula

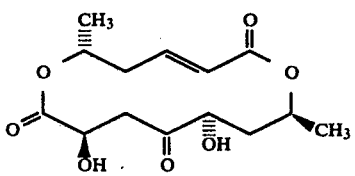

* * * * *